United States Patent
Tedder et al.

(10) Patent No.: US 12,061,197 B2
(45) Date of Patent: Aug. 13, 2024

(54) ***FLAVIVIRUS* DIAGNOSTIC ASSAY**

(71) Applicant: SECRETARY OF STATE FOR HEALTH AND SOCIAL CARE, London (GB)

(72) Inventors: Richard Tedder, Greater London (GB); Steven Dicks, Greater London (GB)

(73) Assignee: Secretary of State for Health and Social Care, London (GB)

( * ) Notice: Subject to any disclaimer, the term of this patent is extended or adjusted under 35 U.S.C. 154(b) by 473 days.

(21) Appl. No.: 16/766,625

(22) PCT Filed: Nov. 23, 2018

(86) PCT No.: PCT/GB2018/053399
§ 371 (c)(1),
(2) Date: May 22, 2020

(87) PCT Pub. No.: WO2019/102215
PCT Pub. Date: May 31, 2019

(65) Prior Publication Data
US 2021/0003572 A1   Jan. 7, 2021

(30) Foreign Application Priority Data
Nov. 24, 2017   (GB) ..................... 1719592

(51) Int. Cl.
*G01N 33/569*   (2006.01)
(52) U.S. Cl.
CPC . *G01N 33/56983* (2013.01); *G01N 2333/185* (2013.01)
(58) Field of Classification Search
None
See application file for complete search history.

(56) References Cited

U.S. PATENT DOCUMENTS 10,837,963 B2 * 11/2020 Steinhagen .......... G01N 33/569
2017/0336404 A1   11/2017 Ali

FOREIGN PATENT DOCUMENTS

| JP | 2009501900 A | 1/2009 |
|---|---|---|
| WO | 2007001737 A2 | 1/2007 |
| WO | 2007/106050 A1 | 9/2007 |
| WO | 2016/022071 A1 | 2/2016 |

(Continued)

OTHER PUBLICATIONS

Search Report mailed Jul. 26, 2018, issued in corresponding United Kingdom Application No. GB1719592.6, filed Nov. 24, 2017, 3 pages.

(Continued)

*Primary Examiner* — Michelle S Horning
(74) *Attorney, Agent, or Firm* — Christensen O'Connor Johnson Kindness PLLC

(57) ABSTRACT

The present invention provides a method for detecting viral infection of a subject by a first *Flavivirus* species, said method comprising: (a) contacting a sample from said subject with a solid phase support, wherein said solid phase support includes a capture means for immobilising antibody present in the sample that binds a first antigen from a first *Flavivirus* species; (b) challenging said immobilised antibody with: (i) a second antigen from a second (different) *Flavivirus* species, wherein the binding of said second antigen thereto suppresses (e.g. blocks) any inherent antigenic binding cross-reactivity towards the second *Flavivirus* species; and (ii) a labelled first antigen from the first *Flavivirus* species, thereby forming a labelled antigen-antibody complex; and (c) wherein the presence of labelled complex indicates viral infection of the subject by the first *Flavivirus* species, and wherein the absence of labelled complex indicates no viral infection of the subject by the first *Flavivirus* species; and kits for performing said method.

20 Claims, 3 Drawing Sheets

(56) References Cited

FOREIGN PATENT DOCUMENTS

| WO | 2017/192756 A1 | 11/2017 |
| WO | 2018/026845 A1 | 2/2018 |
| WO | 2018/197406 A1 | 11/2018 |

OTHER PUBLICATIONS

International Search Report and Written Opinion mailed Feb. 19, 2019, issued in corresponding International Application No. PCT/GB2018/053399, filed Nov. 23, 2018, 14 pages.
Second Written Opinion mailed Nov. 8, 2019, issued in corresponding International Application No. PCT/GB2018/053399, filed Nov. 23, 2018, 6 pages.
International Preliminary Report of Patentability mailed Feb. 3, 2020, issued in corresponding International Application No. PCT/GB2018/053399, filed Nov. 23, 2018, 18 pages.
Bosch, I., et al., "Rapid Antigen Tests for Dengue Virus Serotypes and Zika Virus in Patient Serum," Science Translational Medicine 9(409):eaan1589, Sep. 2017.
Heinz, F.X. and K. Stiasny, "The Antigenic Structure of Zika Virus and Its Relation to Other Flaviviruses: Implications for Infection and Immunoprophylaxis," Microbiology and Molecular Biology Reviews MMBR 31(1):e00055-16, Mar. 2017.
Rice, C.M., et al., "Nucleotide Sequence of Yellow Fever Virus: Implications for Flavivirus Gene Expression and Evolution," Science 229(4715):726-733, Aug. 1985.
Japanese Office Action received for Patent Application No. 2020-528965; mailed on Oct. 5, 2022 (English Translation provided); 22 pages total.

\* cited by examiner

FLAVIVIRUS DIAGNOSTIC ASSAY

The invention relates to an assay for detecting infection of a subject by a *Flavivirus* species (e.g. Zika virus).

The genus *Flavivirus* defines a class of viruses that includes West Nile virus, dengue virus, tick-borne encephalitis, yellow fever virus, and Zika virus. Flaviviruses share several common aspects: size (40-65 nm), appearance (enveloped, icosahedral nucleocapsid), and positive-sense, single-stranded RNA (~10-11 kb).

Most of these viruses are transmitted by the bite of an arthropod (mosquito or tick). Zika virus is a mosquito-borne virus, and is closely related to dengue virus. Although traditionally associated with mild febrile illness, Zika virus has been recently linked with more serious conditions including Guillain-Barre syndrome and foetal microcephaly.

There has been a rapid spread of Zika virus within recent years—over 50 countries currently report active Zika virus transmission. Indeed, in view of its ability to cross to additional mosquito vectors, coupled with a multi-species animal reservoir and other modes of transmission (including sexual and transfusion-based transfer), there is significant potential for further spread. In response, the European Centre for Disease Prevention and Control (ECDC) has advocated an increase in *Flavivirus* testing laboratory capacity in the EU, and the World Health Organisation (WHO) has declared a public health emergency of international concern. There is therefore an urgent and rapidly expanding demand for *Flavivirus* diagnostics.

There are, at present, no FDA-approved diagnostics for identification of Zika virus, though several diagnostic techniques have been authorised temporarily by the FDA under an Emergency Use Authorisation (EUA), for use during the emergency response. Most of the current Zika virus diagnostic assays are RT-PCR based (RealStar® Zika Virus RT-PCR Kit (Altona Diagnostics), Zika Virus RNA Qualitative Real-Time RT-PCR (Focus Diagnostics), and the Trioplex Real-time PT-PCR Assay (CDC).

Whilst existing RT-PCR based methods can provide high levels of sensitivity (with some detecting down to a single genome copy), these methods are only of value for investigation and identification of the acutely infected patient from whom body fluids may be drawn that contain virus genome. Given the short duration of viraemia and the mild clinical symptoms associated with *Flavivirus* infection, very frequently the question of past infection is raised at a time that PCR diagnosis on plasma or blood samples would be unlikely to confirm a diagnosis of recent infection. In addition, from a public health point of view of monitoring *Flavivirus* activity in a population, direct tests for virus are neither adequately sensitive nor cost-effective.

Moreover, a high power requirement significantly reduces portability of PCR-based methods, and can severely limit their suitability for use at the point-of-care (POC) which, in the context of *Flavivirus* virus detection, is often in remote rural locations.

Whilst serological (antibody-based) detection is relatively simple to perform and provides a readout that is easy to understand, existing assays suffer from serious cross-reactivity with related *Flavivirus* species (such as the endemic dengue virus, West Nile virus etc.), or previous immunisation (e.g. yellow fever vaccination), which creates major challenges in positively identifying a particular *Flavivirus* species (e.g. Zika virus) whilst discriminating between other *Flavivirus* species. Furthermore, differential diagnosis based on symptoms alone is not possible, given the similarities in symptoms following infection with any one of these *Flavivirus* species.

There is therefore an urgent and unmet need for a rapid, simple and field-able technology that would enable reliable identification of infection of a subject by a *Flavivirus* species.

The present invention solves one or more of the above-identified problems by providing a flexible, accurate, rapid, robust and sensitive method for detecting infection of a subject by a *Flavivirus* species.

The method of the invention is performed in vitro on a sample (e.g. blood or plasma) taken from a subject, and may be performed directly on said sample. The method is a serological assay, and therefore relies on identification of anti-*Flavivirus* antibody that is present in the sample. The assay provides excellent inter-species discrimination, for example allowing detection of Zika infection in a subject separately infected by dengue virus. In more detail, the method of the present invention typically comprises:

1) a capture step—antibody present in the patient sample that binds to a first antigen from a first *Flavivirus* species is immobilised;
2) a quenching step—the immobilised antibody is challenged with a second antigen from a second (different) *Flavivirus* species, wherein the binding of said second antigen thereto suppresses (e.g. blocks) any inherent antigenic binding cross-reactivity of the immobilised antibody towards the second *Flavivirus* species. This quenching step effectively allows identification of immobilised antibody that specifically binds the first antigen from the first *Flavivirus* species;
3) a binding step to permit detection of antibody that binds to the first antigen from the first *Flavivirus* species—antibody that remains unblocked by the quenching step is challenged with labelled first antigen from the first *Flavivirus* species. In the presence of antibody that binds to the first antigen from the first *Flavivirus* species, labelled first antigen from the first *Flavivirus* species forms a labelled complex. The antibody that binds to the first antigen from the first *Flavivirus* species typically remains immobilised throughout, resulting in a labelled immobilised complex; and
4) a detecting step allows the identification of the presence (or absence) of labelled complex, and thus confirmation the subject has been infected (or not) by the first *Flavivirus* species.

For example, a pregnant subject may be screened for the accurate detection of Zika infection due to the suppression of false-positive dengue detection, and vice versa. Such accurate detection is of vital importance, given the increased risk of the presence of birth defects (e.g. microcephaly) following Zika infection compared to dengue infection, and plays an indispensable role in the decision of future treatment options.

In one aspect the invention provides a method for detecting viral infection of a subject by a first *Flavivirus* species, said method comprising:
  a. contacting a sample from said subject with a solid phase support, wherein said solid phase support includes a capture means for immobilising antibody present in the sample that binds a first antigen from a first *Flavivirus* species;
  b. challenging (e.g. simultaneously or sequentially) said immobilised antibody with:
    i. a second antigen from a second (different) *Flavivirus* species, wherein the binding of said second antigen thereto suppresses (e.g. blocks) any inherent antigenic binding cross-reactivity towards the second *Flavivirus* species; and ii. a labelled first antigen from the first *Flavivirus* species, thereby forming a labelled antigen-antibody complex; and c. wherein the presence of labelled complex (e.g. labelled antigen-antibody complex) indicates viral infection of the subject by the first *Flavivirus* species, and wherein the absence of labelled complex (e.g. labelled antigen-antibody complex) indicates no viral infection of the subject by the first *Flavivirus* species.

In one aspect the invention provides a method for detecting viral infection of a subject by a first *Flavivirus* species, said method comprising:

a. contacting a sample from said subject with a solid phase support, wherein said solid phase support includes a capture means for immobilising antibody present in the sample that binds a first antigen from a first *Flavivirus* species;

b. challenging (e.g. simultaneously or sequentially) said immobilised antibody with:

i. a second antigen from a second (different) *Flavivirus* species, wherein the binding of said second antigen thereto suppresses (e.g. blocks) any inherent antigenic binding cross-reactivity towards the second *Flavivirus* species; and ii. a labelled first antigen from the first *Flavivirus* species, thereby forming a labelled antigen-antibody complex;

c. detecting the presence or absence of labelled complex (e.g. labelled antigen-antibody complex); and d. wherein the presence of labelled complex indicates viral infection of the subject by the first *Flavivirus* species, and wherein the absence of labelled complex indicates no viral infection of the subject by the first *Flavivirus* species.

In one aspect the invention provides a method for detecting viral infection of a subject by a first *Flavivirus* species, said method comprising:

a. contacting a sample from said subject with a solid phase support, wherein said solid phase support includes a capture means for immobilising antibody present in the sample that binds a first antigen from a first *Flavivirus* species;

b. challenging said immobilised antibody with a second antigen from a second (different) *Flavivirus* species, wherein the binding of said second antigen thereto suppresses (e.g. blocks) any inherent antigenic binding cross-reactivity towards the second *Flavivirus* species;

c. challenging said antibody that remains unblocked with labelled first antigen from the first *Flavivirus* species, thereby forming a labelled antigen-antibody complex; and d. wherein the presence of labelled complex (e.g. labelled antigen-antibody complex) indicates viral infection of the subject by the first *Flavivirus* species, and wherein the absence of labelled complex (e.g. labelled antigen-antibody complex) indicates no viral infection of the subject by the first *Flavivirus* species.

In one aspect the invention provides a method for detecting viral infection of a subject by a first *Flavivirus* species, said method comprising:

a. contacting a sample from said subject with a solid phase support, wherein said solid phase support includes a capture means for immobilising antibody present in the sample that binds a first antigen from a first *Flavivirus* species;

b. challenging said immobilised antibody with a second antigen from a second (different) *Flavivirus* species, wherein the binding of said second antigen thereto suppresses (e.g. blocks) any inherent antigenic binding cross-reactivity towards the second *Flavivirus* species;

c. challenging said antibody that remains unblocked with labelled first antigen from the first *Flavivirus* species, thereby forming a labelled antigen-antibody complex;

e. detecting the presence or absence of labelled complex (e.g. labelled antigen-antibody complex); and d. wherein the presence of labelled complex (e.g. labelled antigen-antibody complex) indicates viral infection of the subject by the first *Flavivirus* species, and wherein the absence of labelled complex (e.g. labelled antigen-antibody complex) indicates no viral infection of the subject by the first *Flavivirus* species.

In one aspect the invention provides a method for detecting viral infection of a subject by a first *Flavivirus* species, said method comprising:

a. contacting a sample from said subject with a solid phase support, wherein said solid phase support includes a capture means for immobilising antibody present in the sample that binds a first antigen from a first *Flavivirus* species;

b. challenging (simultaneously or sequentially) said immobilised antibody with:

i. a second antigen from a second (different) *Flavivirus* species, wherein the binding of said second antigen thereto suppresses (e.g. blocks) detection of an antibody having inherent antigenic binding cross-reactivity towards the second *Flavivirus* species (e.g. an antibody that has inherent cross-reactivity to the first and second antigens—preferably an antibody that binds with increased affinity to the second antigen); and ii. a labelled first antigen from the first *Flavivirus* species, thereby forming a labelled antigen-antibody complex; and c. wherein the presence of labelled complex (e.g. labelled antigen-antibody complex) indicates viral infection of the subject by the first *Flavivirus* species, and wherein the absence of labelled complex (e.g. labelled antigen-antibody complex) indicates no viral infection of the subject by the first *Flavivirus* species.

In one aspect the invention provides a method for detecting viral infection of a subject by a first *Flavivirus* species, said method comprising:

a. contacting a sample from said subject with a solid phase support, wherein said solid phase support includes a capture means for immobilising antibody present in the sample that binds a first antigen from a first *Flavivirus* species;

b. challenging (simultaneously or sequentially) said immobilised antibody with:

i. a second antigen from a second (different) *Flavivirus* species, wherein the binding of said second antigen thereto suppresses (e.g. blocks) detection of an antibody having inherent antigenic binding cross-reactivity towards the second *Flavivirus* species (e.g. an antibody that has inherent cross-reactivity to the first and second antigens—preferably an antibody that binds with increased affinity to the second antigen); and ii. a labelled first antigen from the first *Flavivirus* species, thereby forming a labelled antigen-antibody complex;
c. detecting the presence or absence of labelled complex (e.g. labelled antigen-antibody complex); and
d. wherein the presence of labelled complex (e.g. labelled antigen-antibody complex) indicates viral infection of the subject by the first *Flavivirus* species, and wherein the absence of labelled complex (e.g. labelled antigen-antibody complex) indicates no viral infection of the subject by the first *Flavivirus* species.

In one aspect the invention provides a method for detecting viral infection of a subject by a first *Flavivirus* species, said method comprising:
a. contacting a sample from said subject with a solid phase support, wherein said solid phase support includes a capture means for immobilising antibody present in the sample that binds a first antigen from a first *Flavivirus* species;
b. challenging said immobilised antibody with a second antigen from a second (different) *Flavivirus* species, wherein the binding of said second antigen thereto suppresses (e.g. blocks) detection of an antibody having inherent antigenic binding cross-reactivity towards the second *Flavivirus* species (e.g. an antibody that has inherent cross-reactivity to the first and second antigens—preferably an antibody that binds with increased affinity to the second antigen);
c. challenging said antibody that remains unblocked with labelled first antigen from the first *Flavivirus* species, thereby forming a labelled antigen-antibody complex; and
d. wherein the presence of labelled complex (e.g. labelled antigen-antibody complex) indicates viral infection of the subject by the first *Flavivirus* species, and wherein the absence of labelled complex (e.g. labelled antigen-antibody complex) indicates no viral infection of the subject by the first *Flavivirus* species.

In one aspect the invention provides a method for detecting viral infection of a subject by a first *Flavivirus* species, said method comprising:
a. contacting a sample from said subject with a solid phase support, wherein said solid phase support includes a capture means for immobilising antibody present in the sample that binds a first antigen from a first *Flavivirus* species;
b. challenging said immobilised antibody with a second antigen from a second (different) *Flavivirus* species, wherein the binding of said second antigen thereto suppresses (e.g. blocks) detection of an antibody having inherent antigenic binding cross-reactivity towards the second *Flavivirus* species (e.g. an antibody that has inherent cross-reactivity to the first and second antigens—preferably an antibody that binds with increased affinity to the second antigen);
c. challenging said antibody that remains unblocked with labelled first antigen from the first *Flavivirus* species, thereby forming a labelled antigen-antibody complex;
d. detecting the presence or absence of labelled complex (e.g. labelled antigen-antibody complex); and
e. wherein the presence of labelled complex (e.g. labelled antigen-antibody complex) indicates viral infection of the subject by the first *Flavivirus* species, and wherein the absence of labelled complex (e.g. labelled antigen-antibody complex) indicates no viral infection of the subject by the first *Flavivirus* species.

In a preferable embodiment, said second antigen from a second *Flavivirus* species is an unlabelled antigen.

In one aspect, there is provided a kit for detecting viral infection of a subject by a first *Flavivirus* species, said kit comprising:
a. a solid-phase support comprising capture means for immobilising antibody present in the sample that binds a first antigen from a first *Flavivirus* species;
b. a labelled first antigen from a first *Flavivirus* species; and
c. an unlabelled second antigen from a second *Flavivirus* species; wherein the first antigen and the second antigen are inter-species homologs of the same polypeptide/protein, and wherein the first and second *Flavivirus* species are different species.

In one aspect, there is provided a kit for detecting viral infection of a subject by a first *Flavivirus* species, said kit comprising:
a. a solid-phase support comprising capture means for immobilising antibody present in the sample that binds a first antigen from a first *Flavivirus* species;
b. a labelled first antigen from a first *Flavivirus* species; and
c. an unlabelled second antigen from a second *Flavivirus* species;
wherein the first antigen and the second antigen are NS1 protein, and wherein the first and second *Flavivirus* species are different species.

In one aspect, there is provided use of a kit for detecting viral infection of a subject by a first *Flavivirus* species, said kit comprising:
a. a solid-phase support comprising capture means for immobilising antibody present in the sample that binds a first antigen from a first *Flavivirus* species;
b. a labelled first antigen from a first *Flavivirus* species; and
c. an unlabelled second antigen from a second *Flavivirus* species;
wherein the first antigen and the second antigen are inter-species homologs of the same polypeptide/protein, and wherein the first and second *Flavivirus* species are different species.

In one aspect, there is provided use of a kit for detecting viral infection of a subject by a first *Flavivirus* species, said kit comprising:
a. a solid-phase support comprising capture means for immobilising antibody present in the sample that binds a first antigen from a first *Flavivirus* species;
b. a labelled first antigen from a first *Flavivirus* species; and
c. an unlabelled second antigen from a second *Flavivirus* species;
wherein the first antigen and the second antigen are NS1 protein, and wherein the first and second *Flavivirus* species are different species.

Preferably the foregoing aspects allow a distinction to be made between a viral infection in a subject by the first or second *Flavivirus* species by specific detection of infection by the first *Flavivirus* species.

Advantageously, the capture step leads to immobilisation of all antibodies capable of binding to the first *Flavivirus* species. As such, the quenching step can then be adapted based on user requirements by choosing any second antigen desired.

The present invention does not require depletion/removal of cross-reactive antibody, as it provides a much simpler and more reliable quenching step. In one embodiment, a method of the invention does not comprise depleting the sample of an antibody having inherent antigenic binding cross-reactivity towards the second *Flavivirus* species.

The first and second antigens are inter-species homologs of the same polypeptide/protein, and typically demonstrate significant common antibody binding cross-reactivity. Said first and second antigens typically demonstrate at least 60%, at least 70%, at least 80%, or at least 90% sequence identity to each other along their entire length (preferably at least 90% sequence identity to each other along their entire length). Reference to a polypeptide/protein herein embraces fragments thereof having significant common antibody binding cross-reactivity.

The quenching step may comprise challenge of the immobilised antibody with second antigens from two or more second *Flavivirus* species that are different from the first *Flavivirus* species to be detected. Thus, the quenching step may comprise challenge with two, three, four, or more second antigens from two, three, four, or more second *Flavivirus* species. Should two or more second antigens from different second *Flavivirus* species be employed, said two or more second antigens are inter-species homologs of the same polypeptide/protein. Said two or more second antigens typically demonstrate at least 60%, at least 70%, at least 80%, or at least 90% sequence identity to each other along their entire length. Reference to polypeptide/protein herein embraces fragments thereof having significant common antibody binding cross-reactivity.

The first *Flavivirus* species may be selected from any one of West Nile virus, dengue virus (including dengue 1, 2, 3 or 4 virus), tick-borne encephalitis, yellow fever virus, and Zika virus. In a preferred embodiment the first *Flavivirus* species is Zika virus.

The second *Flavivirus* species may be selected from any one of West Nile virus, dengue virus (including dengue 1, 2, 3 or 4 virus), tick-borne encephalitis, yellow fever virus, and Zika virus, though with the proviso that said first and second *Flavivirus* species are different. In a preferred embodiment the second *Flavivirus* species is dengue virus (in particular dengue 3 virus). In one embodiment, the second *Flavivirus* species is dengue virus is one or more selected from dengue 1 virus, dengue 2 virus, dengue 3 virus and dengue 4 virus, or a combination thereof (in such embodiments, said dengue 1, 2, 3 or 4 viruses may be referred to as a second, third, fourth and fifth *Flavivirus* species, respectively).

Preferably, the first *Flavivirus* species is Zika virus and the second *Flavivirus* species is dengue 1, 2, 3 and/or 4 virus. More preferably, the first *Flavivirus* species is Zika virus and the second *Flavivirus* species is dengue virus (in particular dengue 3 virus).

Thus, in one aspect the invention provides a method for detecting viral infection of a subject by a Zika virus, said method comprising:
a. contacting a sample from said subject with a solid phase support, wherein said solid phase support includes a capture means for immobilising antibody present in the sample that binds a first antigen from a Zika virus;
b. challenging (simultaneously or sequentially) said immobilised antibody with:
   i. a second antigen (e.g. NS1) from a dengue virus (e.g. dengue 1, 2, 3 and/or 4 virus), wherein the binding of said second antigen thereto suppresses (e.g. blocks) any inherent antigenic binding cross-reactivity towards the dengue virus; and
   ii. a labelled first antigen from the Zika virus, thereby forming a labelled antigen-antibody complex;
c. detecting the presence or absence of labelled complex (e.g. labelled antigen-antibody complex); and
d. wherein the presence of labelled complex (e.g. labelled antigen-antibody complex) indicates viral infection of the subject by the Zika virus, and wherein the absence of labelled complex (e.g. labelled antigen-antibody complex) indicates no viral infection of the subject by the Zika virus.

The term "suppressing" embraces both reduction of and/or complete blocking of any inherent antigenic binding cross-reactivity towards the second *Flavivirus* species (e.g. reduction of and/or complete blocking of the availability of antibody binding domains (on the immobilised antibody) capable of binding to the second antigen).

The term "immobilising" as used herein may refer to binding with an affinity (measured by the dissociation constant: $K_d$) of at least $10^{-4}$ M, e.g. at least $10^{-5}$ M, $10^{-6}$ M, $10^{-7}$M, $10^{-8}$ M or $10^{-9}$ M. Alternatively or additionally, "immobilising" as used herein may refer to binding with an affinity (measured by way of the association constant $K_a$) of $10^6$ M, e.g. at least $10^7$ M or at least $10^8$ M.

The first antigen and second antigen may be selected from a *Flavivirus* structural protein. For example, the first antigen and second antigen may be the nucleocapsid protein or the envelope protein. Alternatively, the first antigen and second antigen may be selected from a *Flavivirus* non-structural protein. For example, the first antigen and second antigen may be the non-structural protein NS1, the first antigen and second antigen may be the non-structural protein NS2A, the first antigen and second antigen may be the non-structural protein NS2B, the first antigen and second antigen may be the non-structural protein NS3, the first antigen and second antigen may be the non-structural protein NS4A, the first antigen and second antigen may be the non-structural protein NS4B, the first antigen and second antigen may be the non-structural protein NS5, the first antigen and second antigen may be an immune modulator protein, or the first antigen and second antigen may be a protein component of the replication pathway. In more detail reference is made to:
Rice, M. R. et al., (1985), Science vol. 229, p. 726-733;
Heinz, F. X. & Stiasny, K. (2017), Microbiol. and Mol. Biol. Rev. vol. 81, issue 1, p. 1-27; and
Bosch, I. et al., (2017), Sci. Transl. Med., 9, p. 1-13
the content for each of which is hereby incorporated in its entirety by reference thereto.

In a preferred embodiment the first antigen and second antigen is selected from NS1, NS3 or NS5, and is preferably NS1. Thus, in a preferable embodiment the first antigen and second antigen is NS1.

In one embodiment, reference to said second antigen embraces two or more (e.g. 2, 3, 4 or 5) second antigens from two or more (e.g. 2, 3, 4 or 5) second *Flavivirus* species. In such embodiments, said antigens may be referred to as second, third, fourth, fifth etc. antigens and said (different) species may be referred to as second, third, fourth, fifth etc. *Flavivirus* species.

The second antigen may be a conjugate comprising an NS1, NS3 and/or NS5 from each of dengue 1, 2, 3 or 4 virus (e.g. a tetramer conjugate). In one embodiment, the second antigen is a conjugate comprising an NS1 from each of dengue 1, 2, 3 or 4 virus.

In one embodiment, the second antigen is a recombinant protein. In one embodiment, the second antigen is integral to a virus (e.g. viral particle), preferably an attenuated virus.

The quantity of said second antigen used in said challenging (e.g. quenching) step may be between about 1-50 µg, 5-45 µg, 10-40 µg, 15-35 µg, and more preferably 20-30 µg. Suitably, said quantity may be about 25 µg.

Any antigen label may in principle be employed. For example, the label may itself provide an observable/detectable signal (e.g. visible dye), or it may require an activation partner (e.g. horseradish peroxidase (HRPO) plus substrate). Suitably, said label is conjugated directly to the antigen (e.g. by chemical conjugation or as a fusion protein).

Examples of suitable labels include detectable labels such as radiolabels or fluorescent or coloured molecules, enzymatic markers or chromogenic markers—e.g. dyes that provide a visible colour change upon binding of the detection antibody to an antigen. By way of example, the label may be fluorescein-isothiocyanate (FITC), R-phycoerythrin, Alexa Fluor™ 532, CY3 or digoxigenin. The label may be a reporter molecule, which is detected directly, such as by detecting its fluorescent signal, or by exposure of the label to photographic or X-ray film. Alternatively, the label is not directly detectable, but may be detected, for example, in a two-phase system. An example of indirect label detection is binding of an antibody to the label.

In a preferable embodiment, the labelled antigen is labelled with an HRPO. Suitably, said HRPO labelled antigen is detected by means of an activation partner, e.g. a substrate that, when oxidized by HRP using hydrogen peroxide as the oxidizing agent, yields a characteristic color change. Said activation partner may be one or more substrate selected from 3,3',5,5'-Tetramethylbenzidine (TMB), 3,3'-Diaminobenzidine (DAB), 2,2'-azino-bis(3-ethylbenzothiazoline-6-sulphonic acid) (ABTS), o-phenylenediamine dihydrochloride (OPD), 3-amino-9-ethylcarbazole (AEC), Amplex™ Red, Homovanillic acid or Luminol. Preferably, said activation partner is the substrate TMB.

Any solid phase support may in principle be employed. For example, conventional multiwall plates and lateral flow devices.

Any ligand that is able to bind immunoglobulin and leave at least one free Fab binding site (for binding to the first antigen from the first *Flavivirus* species) will provide a suitable capture moiety. This may include any one of a range of different species sourced antibody to Y, a or u Fc or bacterial proteins.

In one embodiment the capture means referred to herein comprises a first antigen from a first *Flavivirus* species. Advantageously, by using a first antigen from a first *Flavivirus* species as a capture means (e.g. in the DABA assay described below) antibodies from different host genera or species can be detected (e.g. using the same assay). Such methods and kits may be considered particularly useful when detecting viral infection in subjects from multiple different genera or species.

In one embodiment the capture means referred to herein comprises an antibody that binds to an antibody (including an antibody that binds to a first *Flavivirus* species) present in a sample from a subject. Suitably, said antibody binds to an Fc region of an antibody (including an antibody that binds to a first *Flavivirus* species) present in a sample from a subject. Preferably the antibody is an anti-human antibody.

The methods of the present invention find utility in detecting either recent (e.g. new) or historic viral infection of a subject by a *Flavivirus*. Discriminating between recent and historic infection may be achieved by determining the type of antibody detected by a method of the invention. Thus, in some embodiments a method of the invention may comprise a step of determining the type of antibody present in a labelled antigen-antibody complex.

In one embodiment the detected antibody is an IgM antibody. IgM is typically the first antibody to appear in response to exposure of a subject to an infection, therefore detection of an IgM antibody may be indicative of a recent (e.g. new, for example within 1 month) infection by a *Flavivirus*. In another embodiment the detected antibody is an IgG antibody. Detection of an IgG antibody may be indicative of a historic (e.g. more than 1 month or 1-2 months after infection) infection by a *Flavivirus*.

The preferred antibody detection formats of the present invention are:

1) DABA (direct antigen bridging assay) in which recombinant first antigen from the first *Flavivirus* species is immobilised on a solid support, and presents to capture any anti-*Flavivirus* antibody present in the subject (patient) sample that binds to said antigen. Bound antibody is then preferably identified via a labelled equivalent of the recombinant first antigen from the first *Flavivirus* species; or
2) Anti-human capture antibody in which said antibody (e.g. rabbit source) is immobilised on a solid support, for example via the Fc region. Said antibody then presents Fab binding domains to capture any human antibody present in the subject sample. Thereafter, bound antibody may be identified via labelled first antigen from the first *Flavivirus* species (as above). The anti-human capture antibody may be selected/designed so that it is, for example, specific for human IgG or human IgM antibodies (as above).

The challenging steps of a method of the invention may be carried out simultaneously or sequentially. In other words the first labelled antigen and second (or further) antigens may be added simultaneously or sequentially.

Suitably, the presence or absence of a labelled antigen-antibody complex is detected via a signal emitted from a label. Preferably, the presence of labelled antigen-antibody complex is confirmed when the signal detected is greater than a signal detected in a control assay, wherein the control assay does not comprise challenging the immobilised antibody with a labelled first antigen.

The signal detected in the control assay may be determined either prior to carrying out a method of the invention or at the same time as carrying out a method of the invention (preferably at the same time).

The skilled person understands that where the methods of the invention comprise a comparison step between two assays (e.g. between a “test assay” and a “control assay”) that conditions (e.g. assay conditions during the method) should be kept consistent. For example, the amount of sample used should be the same, as should the time conditions, etc. Where a comparison is made between two samples herein, suitably the samples are equivalent. For example, the samples being compared may be the same sample types (e.g. blood) and subjected to the same processing steps. Preferably, the samples are obtained from the same subject.

Preferably the first labelled antigen and second (or further) antigens are added simultaneously. Advantageously, such simultaneous challenging allows for the direct competition between second antigen (e.g. cold, unlabelled second antigen) and labelled first antigen for antibody binding sites. The inventors believe that this allows for competition (e.g. fluid phase competition) for antibody binding sites, in which the second antigen out-competes the labelled first antigen for binding to (undesired) immobilised antibody having inherent antigenic binding cross-reactivity towards the second *Flavivirus* species.

In one embodiment, the sample is from a subject, typically an animal, most preferably a human. The terms "subject", "individual" and "patient" are used interchangeably herein.

In such an embodiment, the sample is typically selected from blood (e.g. a dried blood spot), plasma, saliva, serum, sputum, urine, cerebral spinal fluid, semen, cells, a cellular extract, a tissue sample, a tissue biopsy, a stool sample, a swab from any body site and/or one or more organs; typically blood, serum, urine, saliva and/or organ(s).

In one embodiment, the sample is blood. In a preferable embodiment, the sample is serum.

A key advantage to using a blood or serum sample in methods of the present invention is that this sample is readily obtainable from a subject having or suspected of having an infection with a *Flavivirus* species and is obtained with minimal invasiveness.

In one embodiment, the sample is an arthropod (e.g. tick or mosquito) sample. In one embodiment, the sample is a mosquito sample (e.g. a processed mosquito sample). Said mosquito sample may be derived from an *Aedes aegypti*.

In one embodiment, the sample is obtained from surgical or other medical equipment. In one embodiment, the sample is an environmental sample (e.g. water, soil and/or sediment).

In one embodiment a sample may be processed to isolate an antibody from a sample.

In one embodiment, the sample is a crude sample.

In one embodiment, the method is for use in diagnosing an infection with a *Flavivirus* species in a subject. In one embodiment, upon identification of said infection in the subject, the subject is provided with an appropriate treatment or therapy. Said treatment or therapy may be an effective dosage of a medicament to relieve symptoms of infection (e.g. acetaminophen and/or ibuprofen).

The invention is highly-suited to a number of important applications in the detection of antibody to a *Flavivirus* species. For example, the invention can help support local surveillance of antibody to *Flavivirus* species, in the animal reservoir and in humans. This enables rapid targeting of vector control measures including the prediction of emerging *Flavivirus* species epizootics before they enter the human population.

The invention allows the screening of a variety of samples, such as blood, urine, saliva and organs, and can therefore be used to test for suspected cases of infection by a *Flavivirus* species. The invention can also be used in screening travellers returning from an area affected (or an area suspected of being affected) with a particular *Flavivirus* species. The invention can also be used in testing symptomatic subjects and pregnant women, sexual health and family planning screening in affected countries.

The invention is also suitable for diagnosing infection of a subject with a *Flavivirus* species e.g. for confirming whether a subject suspected of being infected with a *Flavivirus* species is indeed infected with said *Flavivirus* species. In one embodiment, the subject is an animal that forms part of the animal reservoir for the virus. In such instances, "infection" refers to a population of a reservoir animal that is supporting the turnover of a *Flavivirus* species.

In one embodiment, a method of the invention may further comprise recording the output of said method on a data readable format.

The term "antibody" (e.g. as it relates to an IgG capture assay of the invention) covers monoclonal antibodies and fragments thereof (e.g. exhibiting the desired biological activity). In one embodiment, an antibody of the present invention is a monoclonal antibody. In one embodiment, the antibody is a fully human monoclonal antibody. In one embodiment, methods of the invention may employ polyclonal antibodies.

In particular, an antibody is a protein including at least one or two, heavy (H) chain variable regions (abbreviated herein as VHC), and at least one or two light (L) chain variable regions (abbreviated herein as VLC). The VHC and VLC regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al, J. Mol. Biol. 196:901-917, 1987). Preferably, each VHC and VLC is composed of three CDRs and four FRs, arranged from amino-terminus to carboxy-terminus in the following order: FRI, CDRI, FR2, DR2, FR3, CDR3, FR4. The VHC or VLC chain of the antibody can further include all or part of a heavy or light chain constant region. In one embodiment, the antibody is a tetramer of two heavy immunoglobulin chains and two light immunoglobulin chains, wherein the heavy and light immunoglobulin chains are interconnected by, e.g., disulfide bonds. The heavy chain constant region includes three domains, CH1, CH2 and CH3. The light chain constant region is comprised of one domain, CL. The variable region of the heavy and light chains contains a binding domain that interacts with an antigen. The term "antibody" includes intact immunoglobulins of types IgA, IgG, IgE, IgD, IgM (as well as subtypes thereof), wherein the light chains of the immunoglobulin may be of types kappa or lambda. The term antibody, as used herein, also refers to a portion of an antibody that binds to one of the above-mentioned markers, e.g., a molecule in which one or more immunoglobulin chains is not full length, but which binds to a marker. Examples of binding portions encompassed within the term antibody include (i) a Fab fragment, a monovalent fragment consisting of the VLC, VHC, CL and CH1 domains; (ii) a F(ab')2 fragment, a bivalent fragment comprising two Fab fragments linked by a disulfide bridge at the hinge region; (iii) a Fc fragment consisting of the VHC and CH1 domains; (iv) a Fv fragment consisting of the VLC and VHC domains of a single arm of an antibody, (v) a dAb fragment (Ward et al, Nature 341:544-546, 1989), which consists of a VHC domain; and (vi) an isolated complementarity determining region (CDR) having sufficient framework to bind, e.g. an antigen binding portion of a variable region. An antigen binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al. (1988) Science IAI-ATi-AIβ; and Huston et al. (1988) Proc. Natl. Acad. Sci. USA 85:5879-5883). Such single chain antibodies are also encompassed within the term antibody. These may be obtained using conventional techniques known to those skilled in the art, and the portions are screened for utility in the same manner as are intact antibodies.

Sequence Identity

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics:1428-1435 (2004). Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

Alignment scores for determining sequence identity

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, ED., John Wiley and Sons, New York (1994), and Hale & Marham, THE HARPER COLLINS DICTIONARY OF BIOLOGY, Harper Perennial, NY (1991) provide the skilled person with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. The headings provided herein are not limitations of the various aspects or embodiments of this disclosure. Amino acids are referred to herein using the name of the amino acid, the three letter abbreviation or the single letter abbreviation. Other definitions of terms may appear throughout the specification. It is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | -1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 1 | 1 | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The percent identity is then calculated as:

$$\frac{\text{Total number of identical matches}}{[\text{length of the longer sequence plus the number of gaps introduced into the longer sequence in order to align the two sequences}]} \times 100$$

ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure. It must be noted that as used herein and in the appended claims, the singular forms "a", "an", and "the" include plural referents unless the context clearly dictates otherwise. Thus, for example, reference to "an antibody" includes a plurality of such candidate agents and reference to "the antibody" includes reference to one or more antibodies and equivalents thereof known to those skilled in the art, and so forth. The publications discussed herein are provided solely for their disclosure prior to the filing date of the present application. Nothing herein is to be construed as an admission that such publications constitute prior art to the claims appended hereto.

The invention will now be described, by way of example only, with reference to the following Examples.

BRIEF DESCRIPTION OF THE DRAWINGS

Embodiments of the invention will now be described, by way of example only, with reference to the following Figures and Examples.

EXAMPLES

Figure 1:
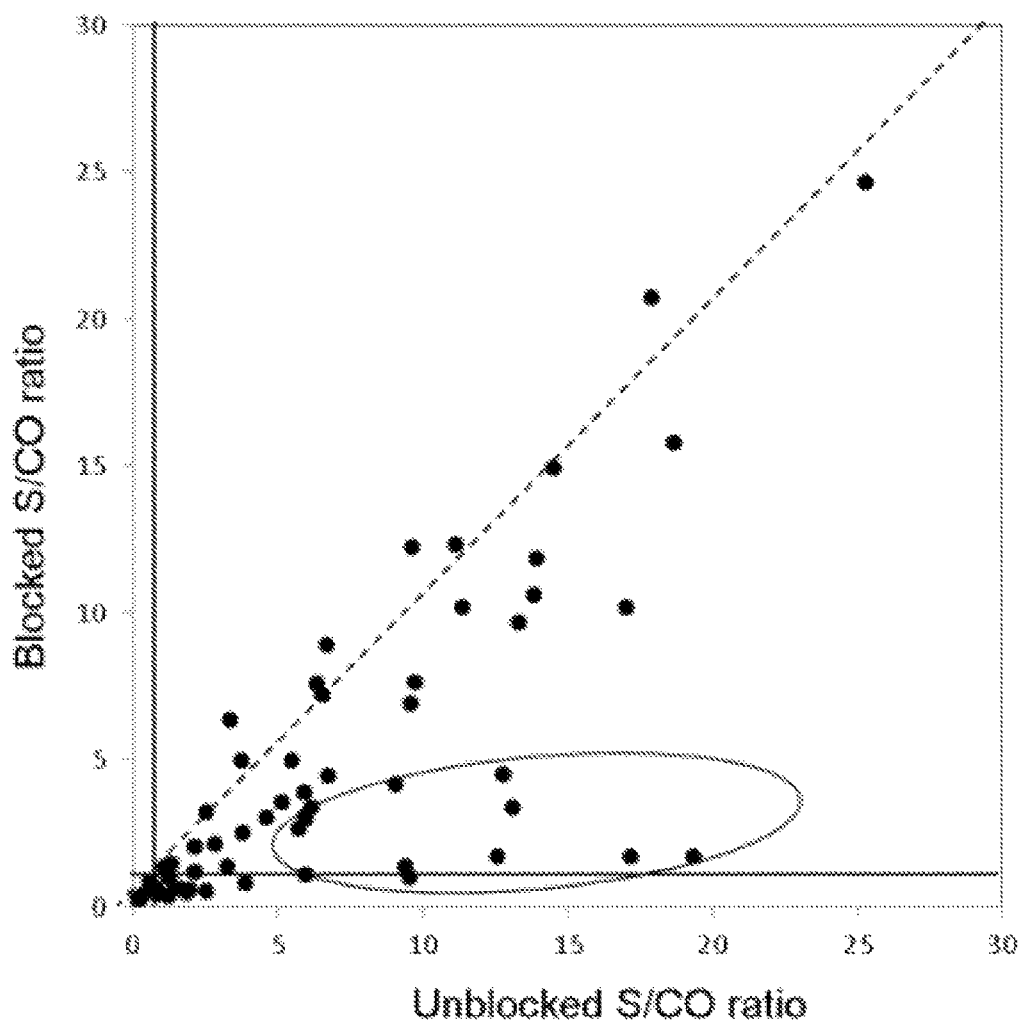
FIG. 1 shows an X by Y plot illustrating the reactivity of 40 serum samples from patients with confirmed acute ZKV infection. Results are derived from a DABA assay of the invention, and are expressed as sample to cut off ratios when tested using un-blocked conjugate diluent and blocked conjugate diluent containing rDV3NS1Ag. Dotted line is a line of interpolated equivalence assuming no difference. The plot displays the reactivity of 40 samples from patients with confirmed ZKV infection using unblocked and blocked conjugate diluents. Samples from patients with proven ZIKA showing a reduced reactivity resulting from the blocked conjugate are circled. S/CO=sample absorbance (S) to cut-off value (CO) ratio.

Double Antigen Bridging Assay (DABA) Kit & Methods

Each kit typically contains sufficient materials for 96 tests. The shelf life of each kit is as indicated on the label fixed to the box containing the kit. It is intended that all components are stored at 2-8° C. unless otherwise stated. Typical 'materials provided' (e.g. in a kit) for performing a method of the invention:

| | |
|---|---|
| Coated Wells: | One plate of 96 wells coated with recombinant ZIKA NS1 antigen. Allow the wells to reach room temperature (18 to 30° C.) before removal from the bag. Place unused wells in the sealable storage bag provided and return to 2-8° C. |
| Negative Control: | One bottle containing 500 μl of Negative Control. Ready to use. |
| Positive Control | One bottle containing 250 μl of Positive Control (purified recombinant monoclonal antibody ZKA35-rIgG1 at a concentration of 0.7 μg/ml). Ready to use. |
| Sample Diluent: | One bottle containing 10 ml of Sample Diluent (coloured 'Green').'Ready to Use |
| Conjugate Diluent: | One bottle containing 10 ml of Conjugate Diluent. Ready to Use. |
| Conjugate Concentrate: | One bottle containing 100 μl of stock 100 times concentrated strength recombinant ZIKA NS1 antigen coupled with horseradish peroxidase in stabiliser solution. Vortex gently then Centrifuge tube to ensure the full volume of Conjugate Concentrate is in bottom of tube prior to opening. Add one volume of Conjugate Concentrate to 99 volumes (ie 1:100 dilution) of required Conjugate Diluent to get the required working strength Conjugate Solution. |
| Additive 'A' | One bottle containing 400 μl of stabiliser solution with no excess Antigen present. |
| Additive 'B' | One bottle containing 300 μl Zika NS1 Antigen diluted 1:1 in stabiliser solution at a final concentration of 250 ug/ml |
| Additive 'C' | One bottle containing 300 μl Dengue3 NS1 Antigen diluted 1:1 in stabiliser solution at a final concentration of 250 ug/ml |
| TMB Substrate-Ready to Use: | One bottle containing 10 ml of 3,3',5,5'- tetramethylbenzidine and stabilisers in a colourless solution (TMB Substrate-ready to use) Keep substrate away from sunlight. The Substrate Solution should be colourless; if it is purple before being used, it should be discarded and fresh Substrate Solution used. Once opened, the bottle of TMB Substrate is stable refrigerated (2-8° C.) for 30 days, but must be discarded if crystals have formed. |

| | |
|---|---|
| Stop Solution (2M $H_2SO_4$: | One bottle containing 5 ml of 2M sulphuric acid ($H_2SO_4$) ready to use. |
| Wash Fluid: | One bottle containing 100 ml of 10 times concentrated strength Wash Buffer Solution. Add one volume of Wash Fluid Concentrate to 9 volumes of distilled or deionised water to give the required volume or dilute the entire contents of one bottle of Wash Fluid to a final volume of 1000 ml. Store the working strength Wash Fluid at 18-30° C. in a closed vessel under which conditions it will retain activity for one month. |

Clean vessels for wash solution preparation
Microtitre plate cover
Micropipettes and disposable tips capable of delivering 200 μL, 100 μL, 20 μL and 1-μL volumes.
Waste discard container with disinfectant
EIA plate reader capable of reading optical density at 450 nm (and 620-650 nm).
Incubator, 37° C.

Specimen Collection & Preparation

Serum and plasma (EDTA, citrated or heparinised) samples are suitable specimens for the test and should be obtained from whole blood using standard laboratory procedure.

Either fresh serum or plasma samples can be used for this assay. If not used immediately, they can be stored at 2-8° C. for one week. Care should be taken to ensure that the serum samples are clear and not contaminated by microorganisms. Plasma samples collected into EDTA, sodium citrate or heparin may be tested, but highly lipaemic, icteric or haemolysed samples should not be used as they can give false results in the assay. Do not heat inactive samples.

Assay Procedure

Step 1: Reagents Preparation

Allow all reagents to reach room temperature (18-30° C.) prior to use.

Check the Wash Buffer concentrate for the presence of salt crystals. If crystals have formed in the solution, re-suspend by warming at 37° C. until the crystals have dissolved. Dilute the stock bottle concentrated wash fluid buffer 10× times with distilled or deionised water. Use a clean vessel to dilute the buffer. It is recommended that working strength buffer be prepared as required on the day of use. Remaining Wash Buffer Concentrate stock should be re-stored at 2-8° C. if not used.

Prepare the 'working strength' Conjugate Solution (see Materials Provided section). In this example twenty four reactive samples, (72 wells in total), can be interrogated, together with the additional plate strip containing the six control wells as follows.

Prepare 3 separate tubes of 'working strength' Conjugate solution with the addition of Additive A, B or C as follows:

Conjugate A Tube—dispense 3.15 ml of working strength Conjugate solution followed by the addition of 350 μl of Additive A (no antigens) to give a total volume of 3.5 ml (volume required for both plate controls and samples). Mix well before Use.

Conjugate B Tube—dispense 2.25 ml of working strength Conjugate solution followed by the addition of 250 μl of Additive B to give a total volume of 2.5 ml containing a molar excess of cold Zika NS1 Antigen (volume required for samples only). Mix well before Use Conjugate C Tube—dispense 2.25 ml of working strength Conjugate solution followed by the addition of 250 μl of Additive C to give a total volume of 2.5 ml containing a molar excess of cold Dengue3 NS1 Antigen (volume required for samples only). Mix well before Use All other reagents are provided ready-to-use.

Step 2: Numbering Wells

Remove and assemble the required number of recombinant ZIKA NS1 antigen coated microwell strips to perform the test. A minimum of 6 wells is optimal for the controls (2× positive controls and 4× negative controls) which are optimally included in each test run. Set the strips needed into strip-holder and only use the required number of strips for the test. (Use the separately provided ZIKA DABA ELISA Front sheet Template to record the sample identity numbers to be tested and procedural information).

Step 3: Adding Controls and Samples

Following a DABA ELISA Frontsheet Template as a guide, pipette 70 μl of Sample diluent and 30 μl of the Positive Control into their respective well positions (1A-1B). Pipette 70 μl of Sample diluent and 30 μl of Negative Control into their respective well positions (1D-1F).

Set up each sample in triplicate to allow the addition of Conjugate A to one well, Conjugate B to a second well and Conjugate C to a third well.

Pipette 70 μl of Sample diluent and 30 μl of each sample into three separate well positions as designated on the DABA ELISA Frontsheet Template (only testing the number of samples in a single test run that can be dispensed into assigned wells within ten minutes—the assay reagent volumes supplied will allow the testing of a total of 24 samples in triplicate.). Note: use a separate disposal pipette tip for each sample, negative control and positive control to avoid cross-contamination.

Step 4: Incubation

Cover the plate with a plate sealer and mix gently by tapping the side of the plate strip holder. Incubate at 37±2° C. in a moist chamber or dry incubator for 60±2 minutes.

Step 5: Washing

After the end of the incubation, remove and discard the plate sealer. Wash each well 5 times with diluted wash buffer (see reagent preparation). The wash cycle is carried out as follows: aspirate the contents of the well and dispense at least 300 μl per well of wash buffer to form a meniscus. Allow the microwells to soak for 30-60 seconds and then aspirate. Repeat the wash cycle a further four times. Alternatively an automatic plate washer may be used. After the final washing cycle turn down the strips plate onto blotting paper or clean towel and tap the plate to remove any remaining wash buffer.

Step 6: Conjugate

Dispense 100 μl of Conjugate A into the 2× Positive control and 4× Negative control well positions (1A-1F)

For each sample tested in triplicate:

Dispense 100 μl of Conjugate A into each sample well one,

Dispense 100 µl of Conjugate B into each sample well two,

Dispense 100 µl of Conjugate C into each sample well three,

Cover the plate with a plate sealer and incubate at 37±2° C. in a moist chamber or dry incubator for 120±2 minutes (If a dry incubator is used do not open the door frequently).

Step 7: Washing

After the end of the incubation, remove and discard the plate sealer. Wash each well 5 times as in Step 5. After the final washing cycle turn down the strips plate onto blotting paper or clean towel and tap the plate to remove any remaining wash buffer Step 8: Substrate Dispense 100 µl of ready to use TMB substrate into each well. This is best performed using a multi-channel pipette.

Cover the plate with a plate sealer and mix gently by tapping the side of the plate strip holder. Incubate the plate at 37±2° C. in a moist chamber or dry incubator for 30 minutes, avoiding light.

The enzymatic reaction between the substrate and conjugate will produce a blue colour in the positive control and any anti-ZIKA positive sample wells.

Step 9: Stopping the Reaction

After the end of the incubation, remove and discard the plate sealer. Add 50 µl of stop solution into each well. This is best performed using a multi-channel pipette and the stop solution should be added using the same timing and sequence that was used to add the substrate solution. Mix gently by tapping the side of the plate strip holder. Following addition of stop solution, an intensive yellow colour will develop in the positive control and any anti-ZIKA positive sample wells.

Step 10: Measure the Absorbance

Calibrate the plate reader with the blank well and read the absorbance at 450 nm within 10 minutes after stopping the reaction (if a dual filter instrument is used, set the reference wavelength at 630 or between 620 and 650 nm on the spectrophotometric plate reader).

Calculate the Cut-Off Value and Evaluate the Results.

Interpretation of Results & Quality Control

Each microplate is optimally considered separately when calculating and interpreting results of the assay, regardless of the number of plates concurrently processed. The results are calculated by relating each sample optical density (OD) value to the cut-off value (CO) of the plate.

Calculation of cut-off value:

$$\text{Cut-off value}(CO) = NC_{mean} + 0.1$$

$NC_{mean}$=the mean absorbance value for 4 negative controls

If one of the negative control values does not meet the Quality Control range specifications, it should be discarded and the mean value calculated again using the remaining values.

Quality Control Range

Each sample absorbance test OD result (S) is valid if the Quality Control criteria are verified as below:

The absorbance value OD of each negative control must be less than 0.100.

The absorbance value OD of each positive control must be greater than 0.800.

Interpretation of Results

Negative results (S/CO≤1): Samples giving an absorbance less or equal to the cut-off value are considered negative, that is, no NS1 antibodies to ZIKA Virus have been detected using this ELISA kit.

Positive results (S/CO>1): Samples giving absorbance greater than the cut-off value are positive for this assay, that is, NS1 antibodies to ZIKA Virus have been detected with this ELISA kit.

Samples containing antibodies specific to Zika NS1 Antigen will be blocked by the addition of Conjugate B, thus will show an absorbance less than the 'sample control well' (wells with the addition of Conjugate A.)

Samples containing antibodies specific to Dengue3 NS1 Antigen will be blocked by the addition of Conjugate C, thus will show an absorbance less than the 'sample control well' (wells with the addition of Conjugate A).

Immunoglobulin G (IgG) Capture Enzyme Immunoassay Kit & Methods

Each kit typically contains sufficient materials for 96 tests. The shelf life of each kit is as indicated on the label fixed to the box containing the kit. All components must be stored at 2 to 8° C. unless otherwise stated.

| | |
|---|---|
| Coated Wells: | One plate of 96 wells coated with anti-human IgG antibody. Allow the wells to reach room temperature (18 to 30° C.) before removal from the bag. Place unused wells in the sealable storage bag provided and return to 2 to 8° C. |
| Transport Medium: | One bottle containing 40 ml of phosphate buffered saline, protein stabiliser and detergent. |
| Negative Control: | One bottle containing 1.8 ml of Negative Control. Ready to Use. |
| Positive Control: | One bottle containing 1 ml of Positive Control (purified recombinant monoclonal antibody ZKA35-rIgG1 at a concentration of 3.56 µg/ml) Ready to Use. |
| Conjugate Diluent: | One bottle containing 10 ml of phosphate buffered saline, protein stabiliser and detergent. |
| Conjugate Concentrate: | One bottle containing 100 µl of stock 100 times concentrated strength recombinant ZIKA NS1 antigen coupled with horseradish peroxidase in stabiliser solution. Vortex gently then Centrifuge tube to ensure the full volume of Conjugate Concentrate is in bottom of tube prior to opening. Add one volume of Conjugate Concentrate to 99 volumes (i.e. 1:100 dilution) of required Conjugate Diluent to get the required working strength Conjugate Solution. |
| Additive 'A' | One bottle containing 400 µl of stabiliser solution with no excess Antigen present. |
| Additive 'B' | One bottle containing 300 µl Zika NS1 Antigen diluted 1:1 in stabiliser solution at a final concentration of 250 ug/ml |
| Additive 'C' | One bottle containing 300 µl Dengue3 NS1 Antigen diluted 1:1 in stabiliser solution at a final concentration of 250 ug/ml |
| TMB Substrate- | One bottle containing 10 ml of 3,3',5,5'-tetramethylbenzidine and |

| Ready to Use: | stabilisers in a colourless solution (TMB Substrate-ready to use) Keep substrate away from sunlight. The Substrate Solution should be colourless; if it is purple before being used, it should be discarded and fresh Substrate Solution used. Once opened, the bottle of TMB Substrate is stable refrigerated (2-8° C.) for 30 days, but must be discarded if crystals have formed. |
|---|---|
| Stop Solution (2M $H_2SO_4$): | One bottle containing 5 ml of 2M sulphuric acid ($H_2SO_4$) ready to use. |
| Wash Fluid: | One bottle containing 100 ml of 10 times concentrated strength Wash Buffer Solution. Add one volume of Wash Fluid Concentrate to 9 volumes of distilled or deionised water to give the required volume or dilute the entire contents of one bottle of Wash Fluid to a final volume of 1000 ml. Store the working strength Wash Fluid at 18-30° C. in a closed vessel under which conditions it will remain fit for purpose for one month. |

Additional Material and Instruments Required (not Part of Kit):

Good quality deionised or distilled water
Clean vessels for wash solution preparation
Microtitre plate cover
Micropipettes and disposable tips capable of delivering 200 μL, 100 μL, 20 μL and 1-5 μl volumes.
Waste discard container with disinfectant
EIA plate reader capable of reading optical density at 450 nm (and 620-650 nm).
Incubator, 37° C.

Specimen Collection & Preparation

Currently serum and plasma (EDTA, citrated or heparinised) samples are suitable specimens for the test and should be obtained from whole blood using standard laboratory procedure.

Either fresh serum or plasma samples can be used for this assay. If not used immediately, they can be stored at 2-8° C. for one week. Care should be taken to ensure that the serum samples are clear and not contaminated by microorganisms. Plasma samples collected into EDTA, sodium citrate or heparin may be tested, but highly lipaemic, icteric or heavily haemolysed samples should not be used as they can give false results in the assay. For optimal results, do not heat inactive samples.

All samples for testing are optimally diluted 1:200 in Transport Medium prior to testing, see below.

Assay Procedure

Step 1: Reagents Preparation

Allow all reagents to reach room temperature (18-25° C.) prior to use.

Check the Wash Buffer concentrate for the presence of salt crystals. If crystals have formed in the solution, re-suspend by warming at 37° C. until the crystals have dissolved. Dilute the stock bottle concentrated wash fluid buffer 10× times with distilled or deionised water. Use a clean vessel to dilute the buffer. It is recommended that working strength buffer be prepared as required on the day of use. Remaining Wash Buffer Concentrate stock should be re-stored at 2-8° C. if not used.

Prepare the 'working strength' Conjugate Solution (see Materials Provided section). In this example twenty four reactive samples, (72 wells in total), can be interrogated, together with the additional plate strip containing the six control wells as follows Prepare 3 separate tubes of 'working strength' Conjugate solution with the addition of Additive A, B or C as follows:

Conjugate A Tube—dispense 3.15 ml of working strength Conjugate solution followed by the addition of 350 μl of Additive A (no antigens) to give a total volume of 3.5 ml (volume required for both plate controls and samples). Mix well before Use.

Conjugate B Tube—dispense 2.25 ml of working strength Conjugate solution followed by the addition of 250 μl of Additive B to give a total volume of 2.5 ml containing a molar excess of cold Zika NS1 Antigen (volume required for samples only). Mix well before Use Conjugate C Tube—dispense 2.25 ml of working strength Conjugate solution followed by the addition of 250 μl of Additive C to give a total volume of 2.5 ml containing a molar excess of cold Dengue3 NS1 Antigen (volume required for samples only). Mix well before Use All other kit reagents are provided ready-to-use.

Dilute the serum or plasma samples 1:200 in Transport Medium by dispensing 2 μl of sample into a labelled tube and adding 400 μl of Transport Medium and mix.

Step 2: Numbering Wells

Remove and assemble the required number of anti-human IgG antibody coated microwell strips to perform the test. A minimum of 6 wells is optimal for the controls (2× positive controls and 4× negative controls) which are optimally included in each test run. Set the strips needed into strip-holder and only use the required number of strips for the test. (Use the separately provided ZIKA G-Capture ELISA Front sheet Template to record the sample identity numbers to be tested and procedural information).

Step 3: Adding Controls and Samples

Following the G-Capture ELISA Frontsheet Template as a guide, pipette 100 μl of the Positive Control into the respective well positions (1A-1B). Pipette 100 μl of the Negative Control into the respective well positions (1D-1F).

Set up each sample in triplicate to allow the addition of Conjugate A to one well, Conjugate B to a second well and Conjugate C to a third well.

Pipette 100 μl of each Sample (pre-diluted 1:200 in Transport Medium) into three separate well positions as designated on the G-Capture ELISA Frontsheet Template (only testing the number of samples in a single test run that can be dispensed into assigned wells within ten minutes—the assay reagent volumes supplied will allow the testing of a total of 24 samples in triplicate.).

Note: use a separate disposal pipette tip for each sample, negative control and positive control to avoid cross-contamination.

Step 4: Incubation

Cover the plate with a plate sealer and mix gently by tapping the side of the plate strip holder. Incubate at 37±2°

C. in a moist chamber or dry incubator for 60±2 minutes (If a dry incubator is used do not open the door frequently).

Step 5: Washing

After the end of the incubation, remove and discard the plate sealer. Wash each well 5 times with diluted wash buffer (see reagent preparation). The wash cycle is carried out as follows: aspirate the contents of the well and dispense at least 300 µl per well of wash buffer to form a meniscus. Allow the microwells to soak for 30-60 seconds and then aspirate. Repeat the wash cycle a further four times. Alternatively an automatic plate washer may be used. After the final washing cycle turn down the strips plate onto blotting paper or clean towel and tap the plate to remove any remaining wash buffer.

Step 6: Conjugate

Dispense 100 µl of Conjugate A into the 2× Positive control and 4× Negative control well positions (1A-1F).

For each sample tested in triplicate:

Dispense 100 µl of Conjugate A into each sample well one,

Dispense 100 µl of Conjugate B into each sample well two,

Dispense 100 µl of Conjugate C into each sample well three.

Cover the plate with a plate sealer and incubate at 37±2° C. in a moist chamber or dry incubator for 30±2 minutes.

Step 7: Washing

After the end of the incubation, remove and discard the plate sealer. Wash each well 5 times as in Step 5. After the final washing cycle turn down the strips plate onto blotting paper or clean towel and tap the plate to remove any remaining wash buffer.

Step 8: Substrate

Dispense 100 µl of ready to use TMB Substrate into each well. This is best performed using a multi-channel pipette.

Cover the plate with a plate sealer and mix gently by tapping the side of the plate strip holder. Incubate the plate at 37±2° C. in a moist chamber or dry incubator for 30±2 minutes, avoiding light.

The enzymatic reaction between the substrate and conjugate will produce a blue colour in the positive control and any anti-ZIKA positive sample wells.

Step 9: Stopping the Reaction

After the end of the incubation, remove and discard the plate sealer. Add 50 µl of Stop Solution into each well. This is best performed using a multi-channel pipette and the stop solution should be added using the same timing and sequence that was used to add the substrate solution. Mix gently by tapping the side of the plate strip holder. Following addition of stop solution, an intensive yellow colour will develop in the positive control and any anti-ZIKA positive sample wells.

Step 10: Measure the Absorbance

Calibrate the plate reader with the blank well and read the absorbance at 450 nm within 10 minutes after stopping the reaction (if a dual filter instrument is used, set the reference wavelength at 630 or between 620 and 650 nm on the spectrophotometric plate reader). Calculate the cut-off value and evaluate the results.

Interpretation of Results & Quality Control

Each microplate is optimally considered separately when calculating and interpreting results of the assay, regardless of the number of plates concurrently processed. The results are calculated by relating each sample optical density (OD) value to the cut-off value (CO) of the plate.

Calculation of cut-off value:

$$\text{Cut-off value}(CO) = NC_{mean} + 0.1$$

$NC_{mean}$=the mean absorbance value for 4 negative controls

If one of the negative control values does not meet the Quality Control range specifications, it should be discarded and the mean value calculated again using the remaining values.

Quality Control Range

Each sample absorbance test OD result (S) is valid if the Quality Control criteria are verified as below:

The absorbance value OD of each negative control must be less than 0.100

The absorbance value OD of each positive control must be greater than 0.800

Interpretation of Results

Negative results (S/CO≤1): Samples giving an absorbance less or equal to the cut-off value are considered negative, that is, no NS1 antibodies to ZIKA Virus have been detected using this ELISA kit.

Positive results (S/CO >1): Samples giving absorbance greater than the cut-off value are positive for this assay, that is, NS1 antibodies to ZIKA Virus have been detected with this ELISA kit.

Samples containing antibodies specific to Zika NS1 Antigen will be blocked by the addition of Conjugate B, thus will show an absorbance less than the 'sample control well' (wells with the addition of Conjugate A.)

Samples containing antibodies specific to Dengue3 NS1 Antigen will be blocked by the addition of Conjugate C, thus will show an absorbance less than the 'sample control well' (wells with the addition of Conjugate A).

Example 1

Double Antigen Bridging Assay (DABA) with the Addition of 'Cold Zika NS1 and Denque3 NS1 Antigen' for the Identification and Blocking of Heterologous Antibodies to Zika Virus NS1 Glycoprotein The experiment carried out in this example followed the DABA methods provided above.

Recombinant Antigen Zika NS1 Coated Plate (MyBiosource) @ 2 µg/ml

Zika NS1 Ag Conjugate (i.e. labelled antigen) to be used at WORKING DILUTION OF 1:40K in Conjugate Diluent (DiaSorin)

Conjugate ONE—stored in Stabiliser at 1:10 Dilution (once removed from −20° C. kept at 4° C.)

Make 1 ml of 1:40K (e.g. 1:40,000) conjugate for strip ONE and 2 ml of 1:20K for strips 2-3

ZIKA NS1 Ag diluted to 1:68 in Conjugate Diluent (DiaSorin)=50 µg/ml (unlabelled antigen)

Dengue 3 NS1 Ag diluted to 1:10 in Conjugate Diluent (DiaSorin)=49 µg/ml (unlabelled antigen)

Positive Control=ZKA35 diluted 1:10K in NHP (0.356 µg/ml)

Negative Control=Normal human plasma samples (English blood donors)

Protocol:

Add 70 µl of Sample Diluent followed by 30 µl of Sample to relevant wells

Incubate for 1 hour at 37°C

Wash ×5 in Wash Buffer (Clin-Tech Ltd)

Add 100 µl of 1:40K Conjugate to strip 1

Add 50 µl of 1:20KConjugate+50 µl of various dilutions of NS1 Antigen OR Dengue 3 Antigen to relevant strips Incubate for 2 hours at 37° C.

Wash ×5 in Wash Buffer (Clin-Tech Ltd)
Add 100 µl of Ready to Use TMB Substrate
Incubate for 30 minutes at 37° ° C.
Add 50 µl stop solution (Clin-Tech Ltd)
The plate was arranged as follows:

| Antigen Addition Conjugate | NONE 100 µl of 1:40K 1 | ZIKA NS1-50 µl of 50 ug/ml 50 µl of 1:20K 2 | D3 NS1-50 µl of 49 ug/ml 50 µl of 1:20K 3 |
|---|---|---|---|
| A | ZK35 (0.356 µg/ml) (positive control) | ZK35 (0.356 µg/ml) (positive control) | ZK35 (0.356 µg/ml) (positive control) |
| B | ZK35 (0.356 µg/ml) (positive control) | ZK35 (0.356 µg/ml) (positive control) | ZK35 (0.356 µg/ml) (positive control) |
| C | NHP (negative control) | NHP (negative control) | NHP (negative control) |
| D | NHP (negative control) | NHP (negative control) | NHP (negative control) |
| E | RS 1700 0093 | RS 1700 0093 | RS 1700 0093 |
| F | RS 1600 5394 | RS 1600 5394 | RS 1600 5394 |
| G | RS 1600 2063 | RS 1600 2063 | RS 1600 2063 |
| H | RS 1600 2616 | RS 1600 2616 | RS 1600 2616 |

Samples E-H are from individuals who have previously been diagnosed to have active ZIKA infection through the demonstration of ZIKA PCR reactive plasma.

The OD measurements at 450/630 nm are presented in Table 1 below:

| | Raw OD read at 450/630 nm | | |
|---|---|---|---|
| | 1 | 2 | 3 |
| A | *1.158* | 0.018 | *1.024* |
| B | *1.004* | 0.026 | *0.906* |
| C | 0.048 | 0.022 | 0.043 |
| D | 0.050 | 0.024 | 0.049 |
| E | *0.960* | 0.060 | *0.478* |
| F | *3.520* | *0.160* | *3.367* |
| G | *2.698* | 0.088 | *2.571* |
| H | *1.068* | 0.044 | *0.957* |
| Pos CTL Mean | 1.081 | 0.022 | 0.965 |
| Neg CTL Mean | 0.049 | 0.023 | 0.046 |
| Cut-Off | 0.149 | 0.123 | 0.146 |

(positive results are underlined and italicised)

The % inhibition was calculated and is presented in Table 2 below:

| Inhibition Percentage by Excess Antigen (50 µg/ml) | | |
|---|---|---|
| | Zika NS1 | Dengue 3 NS1 |
| Positive Control | 98% | 11% |
| Negative Control | N/A | N/A |
| | N/A | N/A |
| RS 1700 0093 | 94% | 50% |
| RS 1600 5394 | 95% | 4% |
| RS 1600 2063 | 97% | 5% |
| RS 1600 2547 | 96% | 10% |

In this table are shown the percentage of the signal reductions displayed in the assay when the quench of each sample's reactivity is either ZIKA NS1 antigen or dengue 3 NS1 antigen. As can be seen there is virtually complete ablation of the signal by the ZIKA antigen indicating that all the moieties that are causing the labelled ZIKA NS1 antigen to bind to the solid-phase are blocked by ZIKA. In comparison in only one of the four convalescent plasmas, RS 1700 0093 does the dengue antigen cause reduction of the signal, in this case by only 50% which indicates that the response to the ZIKA virus infection in this particular individual comprises ZIKA specific antibody of which a component is also present on dengue 3 NS1. A response following ZIKA infection in a patient who has also previously been infected by dengue 3 will comprise specific ZIKA antibody, a component of which will also be displayed on the dengue 3 NS1 antigen.

Example 2

Immunoglobulin G (IgG) Capture Enzyme Immunoassay with the Addition of 'Cold Zika NS1 and Denque3 NS1 Antigen' for the Identification and Blocking of Heterologous Antibodies to Zika Virus NS1 Glycoprotein The experiment carried out in this example followed the IgG Capture Enzyme Immunoassay methods provided above. Specifically, the following were used:

AffiniPure™ Rabbit anti human IgG Coated Plate @ 5 µg/ml

Zika NS1 Antigen Conjugate (MyBiosource) to be used at a working dilution of 1:4K (e.g. 1:1000) in Transport Medium (labelled antigen)

Conjugate ONE—stored in Stabiliser (Clin-Tech Ltd) at 1:10 Dilution (once removed from −20° C. kept at 4° C.)

Positive Control=ZKA35 mAb to be used at 1:1K (e.g. 1:1000) dilution in NHP (3.56 µg/ml)

Negative Control=NHP

ZIKA NS1 Ag diluted to 1:68 in Transport Medium=50 µg/ml (unlabelled antigen)

Dengue 3 NS1 Ag diluted to 1:10 in Transport Medium=49 µg/ml (unlabelled antigen)

Protocol:

Add 100 µl of Samples and Controls—diluted 1:200 in Transport Medium prior to addition to wells Incubate for 1 hour at 37° C.

Wash ×5 in Wash Buffer (Clin-Tech Ltd)

Add 100 µl of 1:4K Conjugate to strip 1

Add 50 µl of ZIKA NS1 Antigen followed by 50 µl of 1:2KConjugate to strip 2

Add 50 µl of DENGUE 3 NS1 Antigen followed by 50 µl of 1:2KConjugate to strip 3

Incubate for 30 minutes at 37° C.

Wash ×5 in Wash Buffer (Clin-Tech Ltd)

Add 100 µl of Ready to Use TMB Substrate

Incubate for 30 minutes at 37° C.

Add 50 µl stop solution (Clin-Tech Ltd)

The plate was arranged as follows:

| Antigen Addition Conjugate | NONE 100 µl of 1:4K 1 | Zika NS1-50 µl of 50 ug/ml 50 µl of 1:2K 2 | D3 NS1-50 µl of 49 ug/ml 50 µl of 1:2K 3 |
|---|---|---|---|
| A | ZK35 1:1K (3.56 µg/ml) (positive control) | ZK35 1:1K (3.56 µg/ml) (positive control) | ZK35 1:1K (3.56 µg/ml) (positive control) |
| B | ZK35 1:1K (3.56 µg/ml) (positive control) | ZK35 1:1K (3.56 µg/ml) (positive control) | ZK35 1:1K (3.56 µg/ml) (positive control) |
| C | NHP (negative control) | NHP (negative control) | NHP (negative control) |
| D | NHP (negative control) | NHP (negative control) | NHP (negative control) |
| E | RS 1700 0093 | RS 1700 0093 | RS 1700 0093 |
| F | RS 1600 5394 | RS 1600 5394 | RS 1600 5394 |

-continued

| Antigen Addition Conjugate | NONE 100 μl of 1:4K 1 | Zika NS1-50 μl of 50 ug/ml 50 μl of 1:2K 2 | D3 NS1-50 μl of 49 ug/ml 50 μl of 1:2K 3 |
|---|---|---|---|
| G | RS 1600 2063 | RS 1600 2063 | RS 1600 2063 |
| H | RS 1600 2547 | RS 1600 2547 | RS 1600 2547 |

Samples E-H are from individuals who have previously been diagnosed to have active ZIKA infection through the demonstration of ZIKA PCR reactive plasma.

The OD measurements at 450/630 nm are presented in Table 3 below:

| | Raw OD read at 450/630 nm | | |
|---|---|---|---|
| | 1 | 2 | 3 |
| A | *1.588* | 0.054 | *1.560* |
| B | *1.615* | 0.051 | *1.555* |
| C | 0.064 | 0.050 | 0.048 |
| D | 0.058 | 0.042 | 0.048 |
| E | *0.280* | 0.056 | 0.106 |
| F | *1.671* | 0.111 | *0.871* |
| G | *0.384* | 0.051 | *0.351* |
| H | *0.541* | 0.061 | *0.496* |
| Pos CTL Mean | 1.602 | 0.053 | 1.558 |
| Neg CTL Mean | 0.061 | 0.046 | 0.048 |
| Cut-Off | 0.161 | 0.146 | 0.148 |

(positive results above the 'cut-off' value are underlined and italicised)

The % inhibition was calculated and is presented in Table 4 below:

| | Inhibition Percentage by Excess Antigen (50 μg/ml) | |
|---|---|---|
| | Zika NS1 | Dengue 3 NS1 |
| Positive Control | 97% | 3% |
| Negative Control | N/A | N/A |
| | N/A | N/A |
| RS 1700 0093 | 80% | 62% |
| RS 1600 5394 | 93% | 48% |
| RS 1600 2063 | 87% | 9% |
| RS 1600 2547 | 89% | 8% |

These data demonstrate that the addition of the ZIKA NS1 antigen in the blocking step quenches the signal generated by convalescent plasma in the G capture assay and that a component of the signal is also carried on dengue 3 NS1 antigen but that the inhibition is best achieved by the ZIKA NS1 antigen.

Example 3

Demonstration of Suppression of Antigenic Binding Cross-Reactivity Towards Dengue Virus Antigen in Samples Derived from ZIKA Patients This example relates to the performance of an assay of the invention on a set of samples from subjects undergoing acute ZIKA infection. Said subjects were confirmed to have a ZIKA infection by PCR and their subsequent follow-up. In this experiment, conducted early in the field, the reactivity of the subject samples (sera) was measured in the DABA capture assay in two formats—(i) using the 'unblocked conjugate' format where the conjugate contained only HRPO-labelled ZIKA (i.e. absent a quenching step) or (ii) using the 'blocked' format where the immobilised antibodies having cross-resistance to dengue are blocked/quenched (i.e. using the conjugate modified by addition of quenching dengue virus NS1 antigen)—see FIG. 1.

Figure 2:
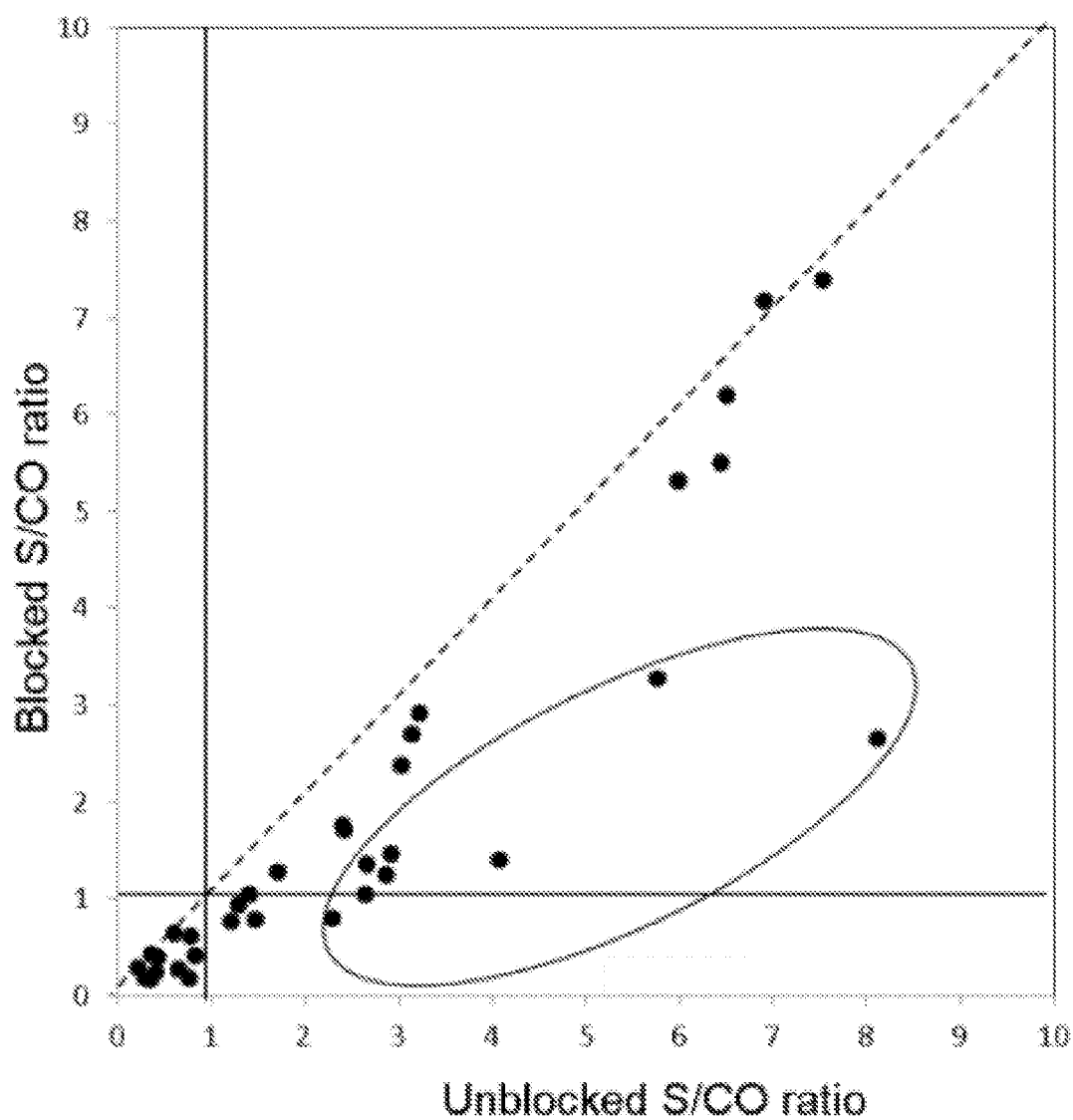
FIG. 2 shows an X by Y plot illustrating the reactivity of 36 serum samples from patients with confirmed acute ZKV infection (these samples were also used in the assay demonstrated in FIG. 1). Results are derived from an IgG capture assay of the invention, and are expressed as sample to cut off ratios when tested using un-blocked conjugate diluent and blocked conjugate diluent containing rDV3NS1Ag. Dotted line is a line of interpolated equivalence assuming no difference. The plot displays the reactivity of 36 samples from patients with confirmed ZKV infection using unblocked and blocked conjugate diluents. Samples from patients with proven ZIKA showing a reduced reactivity resulting from the blocked conjugate are circled.

For comparative purposes, the same samples were testing in an IgG capture assay in both the unblocked conjugate and blocked formats—see FIG. 2.

For both the DABA and IgG capture assays, a significant decrease in the reactivity of samples containing cross-reactive antibodies was observed in the blocked format. This demonstrates successful application of the invention in the suppression of antigenic binding cross-reactivity towards dengue virus antigen in samples derived from ZIKA patients.

Example 4

Demonstration of Prevention of False-Positive ZIKA Virus Detection in Patient Samples A set of 20 patient samples (sera) was assembled, which were demonstrated previously to have strong reactivity for anti-dengue virus antibody, and that were also reactive in both the DABA and IgG capture assays for the detection of anti-ZIKA antibodies.

Figure 3:
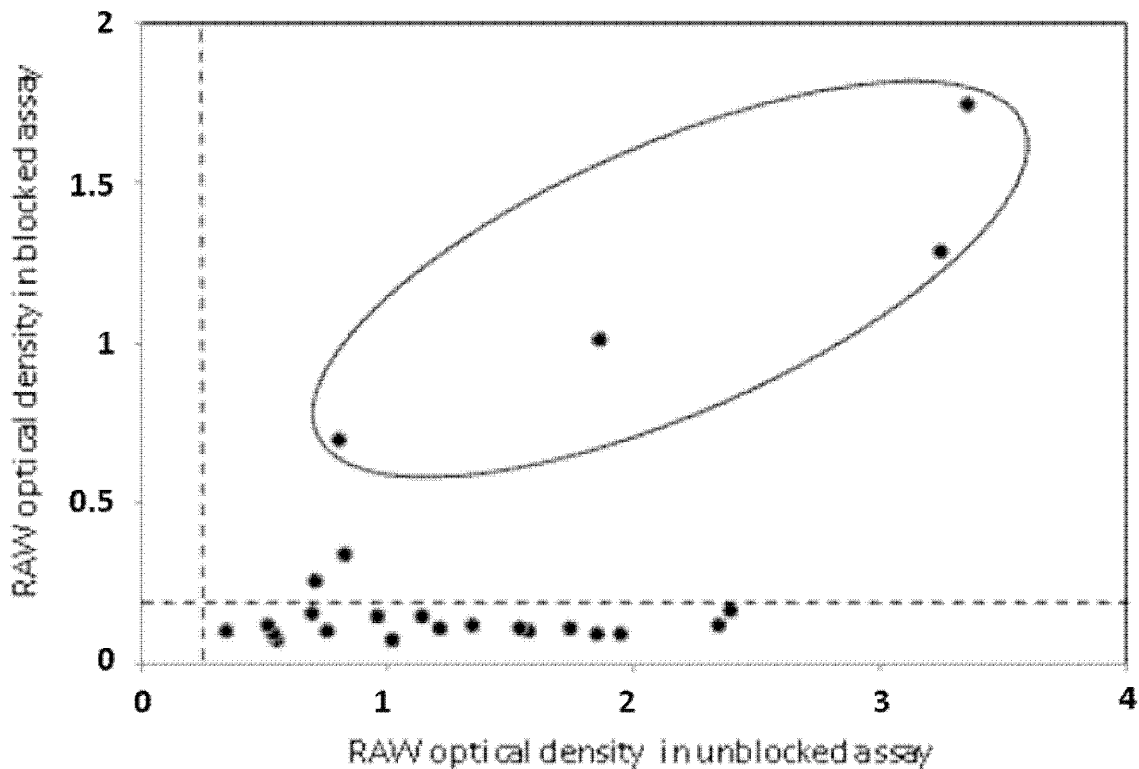
FIG. 3 shows an X by Y plot illustrating the reactivity of 20 serum samples from patients with confirmed dengue infection. Results are derived from an IgG capture assay of the invention, and are expressed as Raw Optical Densities (ODs) when tested using un-blocked conjugate diluent and blocked conjugate diluent containing rDVmixedNS1Ag. The plot displays the reactivity of samples from patients not infected by ZIKA whose serum reacted with ZIKA antigen NS1Ag using unblocked and blocked conjugate diluents. Control samples from patients recovering from proven ZIKA are circled.

Panel samples were tested in an IgG capture assay as before (for detection of ZIKA) in both the 'unblocked conjugate' format (containing only HRPO labelled ZIKA NS1 antigen) or the 'blocked' format (containing a quenching mixture of Dengue types 1-4 inclusive NS1 antigen)—see FIG. 3.

Figure 4:
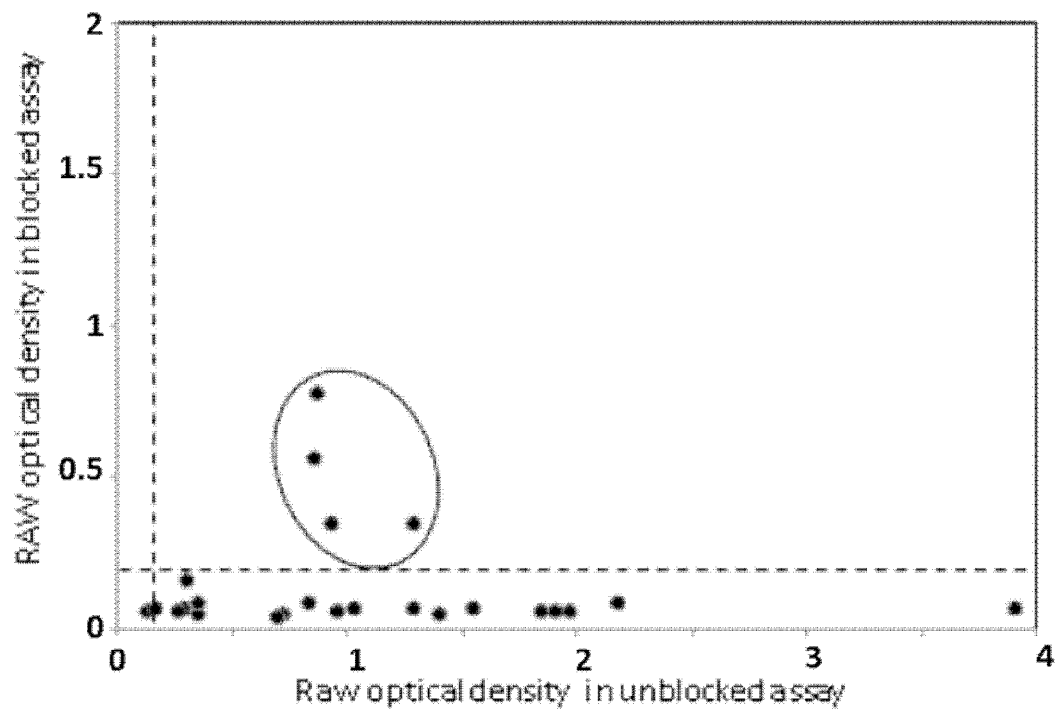
FIG. 4 shows an X by Y plot illustrating the reactivity of 20 serum samples from patients with confirmed dengue infection (the same samples as used in the assay demonstrated in FIG. 4). Results are derived from a DABA assay of the invention, and are expressed as Raw Optical Densities (ODs) when tested using un-blocked conjugate diluent and blocked conjugate diluent containing rDVmixedNS1Ag. The plot displays the reactivity of samples from patients not infected by ZIKA whose serum reacted with ZIKA antigen NS1Ag using unblocked and blocked conjugate diluents. Control samples from patients recovering from proven ZIKA are circled.

For comparative purposes, the same samples were testing in a DABA assay in both the unblocked conjugate and blocked formats—see FIG. 4.

In both assays, control samples were included from patients recovering from proven ZIKA infection (circled).

For both the DABA and IgG capture, a significant decrease in the reactivity of the samples was observed in the blocked format. This demonstrates successful application of the invention in preventing false-positive detection of ZIKA samples.

Importantly, the detection of genuine ZIKA infection was not impeded, demonstrating the utility of the invention in the detection of ZIKA while preventing false-positive detection.

One of the principal concerns has been whether the blocking of spurious reactivity in a conjugate can have an impact on the sensitivity of an assay for detecting antibody to ZIKA. In both the DABA and the IgG capture assay the addition of ZIKA antigen reveals that some sera from patients undergoing PCR proven ZIKA virus infection clearly have pre-existing dengue Ab, not surprising given the co-circulation of these viruses in endemic countries. Data in both FIG. 1 and FIG. 2 demonstrate that there are sera whose reactivity is particularly reduced by the addition of blocking dengue antigen. Given that antibody to dengue is very common it is not a surprising observation.

In a subsequent analysis, using a quadrivalent dengue antigen pool to provide the blocking activity it can be seen that in the IgG capture assay the reactivity of all but two of the cross-reactive "false positive" samples is entirely quenched (FIG. 3). Interestingly the low level control positive ZIKA antibody-containing samples remain clearly detectable. In the DABA assay the false reactivity of all 20 samples is quenched with the control positive samples clearly visible.

These data support the use of a quenching component in the blocked conjugate which preserves the ability to detect ZIKA specific antibody whilst preventing spurious cross reactivity.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method for detecting a viral infection of a subject by a first *Flavivirus* species, said method comprising:

a. contacting a sample from said subject with a solid phase support, wherein said solid phase support includes a capture means for immobilising an antibody present in the sample that binds a first antigen from a first *Flavivirus* species;

b. challenging said immobilised antibody with a second antigen from a second *Flavivirus* species, wherein the binding of said second antigen thereto suppresses any inherent antigenic binding cross-reactivity towards the second *Flavivirus* species; and c. challenging the antibody that remains unblocked with labelled first antigen from the first *Flavivirus* species, thereby forming a labelled antigen-antibody complex;

wherein the presence of labelled complex indicates viral infection of the subject by the first *Flavivirus* species, and wherein the absence of labelled complex indicates no viral infection of the subject by the first *Flavivirus* species;

wherein the first and second antigens are inter-species homologs of the same polypeptide/protein.

2. The method of claim 1, wherein said challenging steps are carried out simultaneously or sequentially.

3. The method of claim 1, wherein said challenging steps are carried out simultaneously.

4. The method of claim 1, wherein said second antigen is unlabelled.

5. The method of claim 1, wherein the capture means for immobilising an antibody that binds a first antigen from a first *Flavivirus* species comprises a first antigen from a first *Flavivirus* species bound to the solid phase support.

6. The method of claim 1, wherein the capture means for immobilising an antibody that binds a first antigen from a first *Flavivirus* species comprises an anti-human antibody that binds to an Fc region of the antibody that binds a first antigen from a first *Flavivirus* species.

7. The method of claim 1, wherein the first antigen from the first *Flavivirus* species is a Zika virus antigen.

8. The method of claim 7, wherein the second antigen is a non-Zika *Flavivirus* species antigen, and wherein the presence of labelled complex indicates viral infection of the subject by a Zika virus species, and wherein the absence of labelled complex indicates no infection of the subject by the Zika virus species.

9. The method of claim 1, wherein the second antigen from the second *Flavivirus* species is a Dengue virus antigen.

10. The method of claim 1, wherein the antibody of the labelled antibody-antigen complex is an IgG antibody.

11. The method of claim 1, wherein the antibody of the labelled antibody-antigen complex is an IgM antibody.

12. The method of claim 1, further comprising recording the output of said method on a data readable format.

13. A kit for detecting viral infection of a subject by a first *Flavivirus* species, said kit comprising:

a. a solid-phase support comprising capture means for immobilising an antibody present in a sample that binds a first antigen from a first *Flavivirus* species;

b. a labelled first antigen from a first *Flavivirus* species; and c. an unlabelled second antigen from a second *Flavivirus* species;

wherein the first antigen and the second antigen are NS1 proteins, and wherein the first and second *Flavivirus* species are different species;

wherein the first and second antigens are inter-species homologs of the same polypeptide/protein.

14. The kit of claim 13, wherein the capture means for immobilising an antibody present in the sample that binds a first antigen from a first *Flavivirus* species comprises an immobilised first antigen from a first *Flavivirus* species.

15. The kit of claim 13, wherein the capture means for immobilising an antibody present in the sample that binds a first antigen from a first *Flavivirus* species comprises an anti-human antibody that binds the Fc region of antibody present in the sample that binds a first antigen from a first *Flavivirus* species.

16. The kit of claim 13, wherein the first *Flavivirus* species is a Zika virus.

17. The kit of claim 13, wherein the unlabelled second *Flavivirus* species is a dengue virus.

18. The kit of claim 13, further comprising instructions for use.

19. The method of claim 8, wherein the absence of labelled complex indicates infection by a different non-Zika *Flavivirus* species.

20. The method of claim 9, wherein the Dengue virus antigen is a dengue 3 virus antigen.

* * * * *